United States Patent
Walls et al.

(10) Patent No.: US 6,390,975 B1
(45) Date of Patent: May 21, 2002

(54) APPARATUS AND METHODS FOR PERFORMING OTOSCOPIC PROCEDURES

(75) Inventors: Richard Walls, deceased, late of Tacoma, WA (US); by Margaret A. Larsen, legal representative, Little Falls; by Sharon A. Goodman, legal representative, Plymouth, both of MN (US); Mark Grubb, Edgewood, WA (US); Steve Burrows; Chris Burrows, both of Kent, WA (US); Steve Hunt, Diamond Bar, CA (US)

(73) Assignee: Walls Precision Instruments, LLC, Casper, WY (US)

( * ) Notice: Subject to any disclaimer, the term of this patent is extended or adjusted under 35 U.S.C. 154(b) by 31 days.

(21) Appl. No.: 09/604,934

(22) Filed: Jun. 27, 2000

Related U.S. Application Data

(63) Continuation-in-part of application No. 09/118,144, filed on Jul. 16, 1998, now abandoned.

(51) Int. Cl.[7] .............................................. A61B 1/227
(52) U.S. Cl. ...................................................... 600/200
(58) Field of Search ................................ 600/184, 199, 600/200

(56) References Cited

U.S. PATENT DOCUMENTS

| | | | |
|---|---|---|---|
| 672,317 A | 4/1901 | Dow | |
| 1,775,140 A | 9/1930 | Platou | |
| 3,020,912 A | 2/1962 | Chester | |
| 3,596,653 A | * 8/1971 | Hotchkiss | 600/200 |
| 3,848,587 A | 11/1974 | McDonald | |
| 3,949,740 A | * 4/1976 | Twentier | 600/200 |
| 4,335,713 A | 6/1982 | Komiya | |
| 4,380,998 A | 4/1983 | Kieffer, III et al. | |
| 4,641,663 A | 2/1987 | Juhn | |
| 4,785,796 A | 11/1988 | Mattson | |
| 4,913,132 A | 4/1990 | Gabriel | |
| 5,363,839 A | 11/1994 | Lankford | |
| 5,390,663 A | 2/1995 | Schaefer | |
| 5,392,764 A | 2/1995 | Swanson et al. | |
| 5,709,677 A | 1/1998 | Slatkline | |
| 5,711,309 A | 1/1998 | Goldenberg | |
| 5,916,150 A | 6/1999 | Sillman | |

* cited by examiner

Primary Examiner—Eduardo C. Robert
(74) Attorney, Agent, or Firm—Seed IP Law Group PLLC

(57) ABSTRACT

An otoscopic accessory for use in performing procedures in the external auditory canal and middle ear space, having a speculum, a probe and an actuator. The speculum has a generally tapered sidewall. The proximal end of the sidewall is configured to engage the head of an otoscope, and the distal end of the sidewall is configured to be inserted into a patient's outer ear canal. The probe has a shaft that is positioned against an exterior surface of the sidewall of the speculum. The actuator is coupled at its distal portion to the speculum. The distal portion of the actuator is closely conformed to the proximal end of the sidewall of the speculum to form a guide between the exterior surface of the speculum and the distal portion of the actuator. The probe is positioned within the guide, and the guide directs the distal end of the probe to a location within or on the distal end of the sidewall of the speculum. The probe is fixed to and moves with the proximal portion of the actuator. The actuator moves with the probe between a first position in which the distal end of the probe is proximal of the distal end of the sidewall of the speculum, and a second position in which the distal end of the probe projects beyond the distal end of the sidewall of the speculum. The practitioner can thus manipulate the actuator while the speculum is engaged with the patient's outer ear canal to cause the probe to project toward or through the patient's eardrum.

45 Claims, 11 Drawing Sheets

APPARATUS AND METHODS FOR PERFORMING OTOSCOPIC PROCEDURES

CROSS-REFERENCE TO RELATED APPLICATION

This application is a continuation-in-part of U.S. patent application Ser. No. 09/118,144 filed Jul. 16, 1998, which has abandoned since the filing of this application.

TECHNICAL FIELD

The present invention is directed toward apparatus and methods for performing medical procedures. More particularly, the present invention is directed toward apparatus and methods for performing medical procedures in the external auditory canal and the middle ear space.

BACKGROUND OF THE INVENTION

The otoscope has long been the instrument of choice of medical practitioners for diagnosis of a variety of ear ailments. Used in conjunction with a standard ear speculum, the otoscope allows the user an illuminated, magnified view of the external auditory canal (a.k.a. the ear canal) and tympanic membrane (a.k.a. the eardrum).

Otoscopes are commonly used to diagnose middle ear infections, which are indicated by various physical findings associated with the buildup of trapped fluid behind the eardrum. Prior to the antibiotic era, medical practitioners commonly treated middle ear infections by incising or puncturing the eardrum with a handheld probe inserted through an otoscope head. This procedure, called myringotomy or tympanocentesis, was meant to promote healing and relieve discomfort by allowing the fluid trapped within the middle ear to drain into the external auditory canal. An unobstructed view of the probe and the eardrum is very important during this procedure in allowing the practitioner to make the incision at the proper location on the eardrum. For similar reasons, fine control of the movement of the probe is also very important. Likewise, maintaining the patient's head in a fixed position is also important to performing this procedure.

This traditional method was associated with a number of disadvantages. First, the practitioner's view was often hindered by the removal of the magnifying lens to admit an instrument through the otoscope head. Second, the presence of the instrument within the otoscope head often obstructed the practitioner's view through the otoscope into the ear canal. Third, no mechanical control feature was available to guide the handheld probe into the middle ear space, or to limit its insertion distance. Finally, the practitioner was unable to directly monitor or control movement of the patient's head, as one hand was required to manipulate the otoscope and the other to manipulate the probe.

During the latter half of the 20th century, as antibiotics gained acceptance, tympanocentesis fell into disfavor as a treatment option for middle ear infections.

Modern medical practitioners are now faced with evidence of increasing emergence of antibiotic resistant bacteria. Treatment guidelines for bacterial infections consequently are being carefully reviewed and revised in a global effort to stem the advancement of antibiotic resistance. Middle ear infections, which currently account for approximately 25% of all oral antibiotic prescriptions in the U.S., are a prime target in this effort.

It is known that middle ear infections, which are accompanied by fluid trapped in the middle ear space, can have either a viral or bacterial etiology. Furthermore, some cases wherein fluid is trapped in the middle ear are not accompanied by an infection at all. Rather, the trapped fluid is sterile. Antibiotics will have no effect on viral ear infections, or on ear ailments where no infection exists.

Once bacterial etiology has been established, optimum medical treatment for an infection requires positive identification of the causative organism and its specific antibiotic susceptibilities. In middle ear infections, etiological and bacterial identification is typically made by obtaining a sample of middle ear fluid for culture analysis. In spite of the inherent complicated nature of the procedure, tympanocentesis is gaining recognition as a necessary supplement to the use of antibiotics.

SUMMARY OF THE INVENTION

The present invention relates to apparatus that can be used in combination with an otoscope for performing procedures in the external auditory canal and the middle ear space, and to methods of making such apparatus. In one embodiment, a speculum having a tapered sidewall is configured at its proximal end for engagement with the otoscope, and at its distal for insertion into the ear canal. The exterior surface of the sidewall has a groove extending from the proximal end of the sidewall toward the distal end of the sidewall. The sidewall also has an opening, located distally of the groove and aligned with the groove. The groove is sized and shaped to allow a practitioner to place a probe against the proximal end of the sidewall and slide the probe along the groove, through the opening in the sidewall, and into the ear canal. Using the apparatus, the practitioner can view the ear canal and eardrum through the speculum while inserting the probe along the exterior wall of the speculum. The practitioner accordingly can puncture the eardrum using the probe without the probe obscuring the practitioner's view of the procedure.

In another embodiment of the invention, the speculum also incorporates one or more slots adjacent the groove that are sized and shaped to receive complementary tabs on an actuator. The actuator carrying a needle or probe can be placed against the sidewall of the speculum with the needle urged against the groove, then snapped into place in the slots. The needle accordingly does not need to be threaded into the system. The actuator can assist the practitioner in controllably inserting the probe or needle into the ear canal and performing the procedure.

In still another embodiment of the present invention, the actuator incorporates an insertion-distance regulator and a biasing means. The distance regulator prevents the actuator from projecting the probe more than a maximum distance beyond the distal end of the speculum. The biasing means retracts the needle upon release of pressure on the actuator, and returns the needle to a location internal to the speculum.

In yet another embodiment of the present invention, the actuator is oriented with respect to the speculum to position the practitioner's one hand directly over the side of the patient's head to facilitate the practitioner in monitoring and controlling movement of the patient's head. This and other embodiments can incorporate a hollow probe or needle coupled to a bulb for generating a suction. The bulb can be attached to the needle by a flexible tube allowing the bulb to be held with the practitioner's other hand, which also holds the base of the otoscope, and which also can assist in monitoring and controlling the patient's head. Consequently, the practitioner can perform the entire procedure and draw a sample of fluid from the middle ear, while holding the patient's head still, without the assistance of any additional individuals or mechanical equipment.

In yet another embodiment of the present invention, the speculum is adapted for use in combination with both currently common types of otoscope heads. The proximal end of the speculum has a generally cylindrical projection sized and shaped to engage a mouth on a first type of otoscope head. The internal surface of the speculum has a number of ribs contoured to conform with the distal end of a second, or diagnostic type, otoscope head. A tab or prong projecting from the internal surface of the speculum engages a locking groove on the second type of otoscope head. As a result, the same speculum can be used by the practitioner regardless of the type of otoscope being used.

DETAILED DESCRIPTION OF THE ILLUSTRATED EMBODIMENTS

The present invention is generally directed toward apparatus for performing medical procedures in the external auditory canal and middle ear space, and to methods of making such apparatus. Several embodiments of the invention allow a medical practitioner to view the ear canal and eardrum, to controllably insert a needle or probe into the ear canal and puncture the eardrum, to draw fluid from the middle ear, and to retain the patient's head in a fixed position. The present invention can allow a single person to perform all of these functions without the necessary help from others. Many specific details of certain embodiments of the invention are set forth in the following description and in FIGS. 1–19 to provide a thorough understanding of such embodiments. One skilled in the art, however, will understand that the present invention may have additional embodiments, or may be practiced without several of the details described in the following description.

Figure 1:
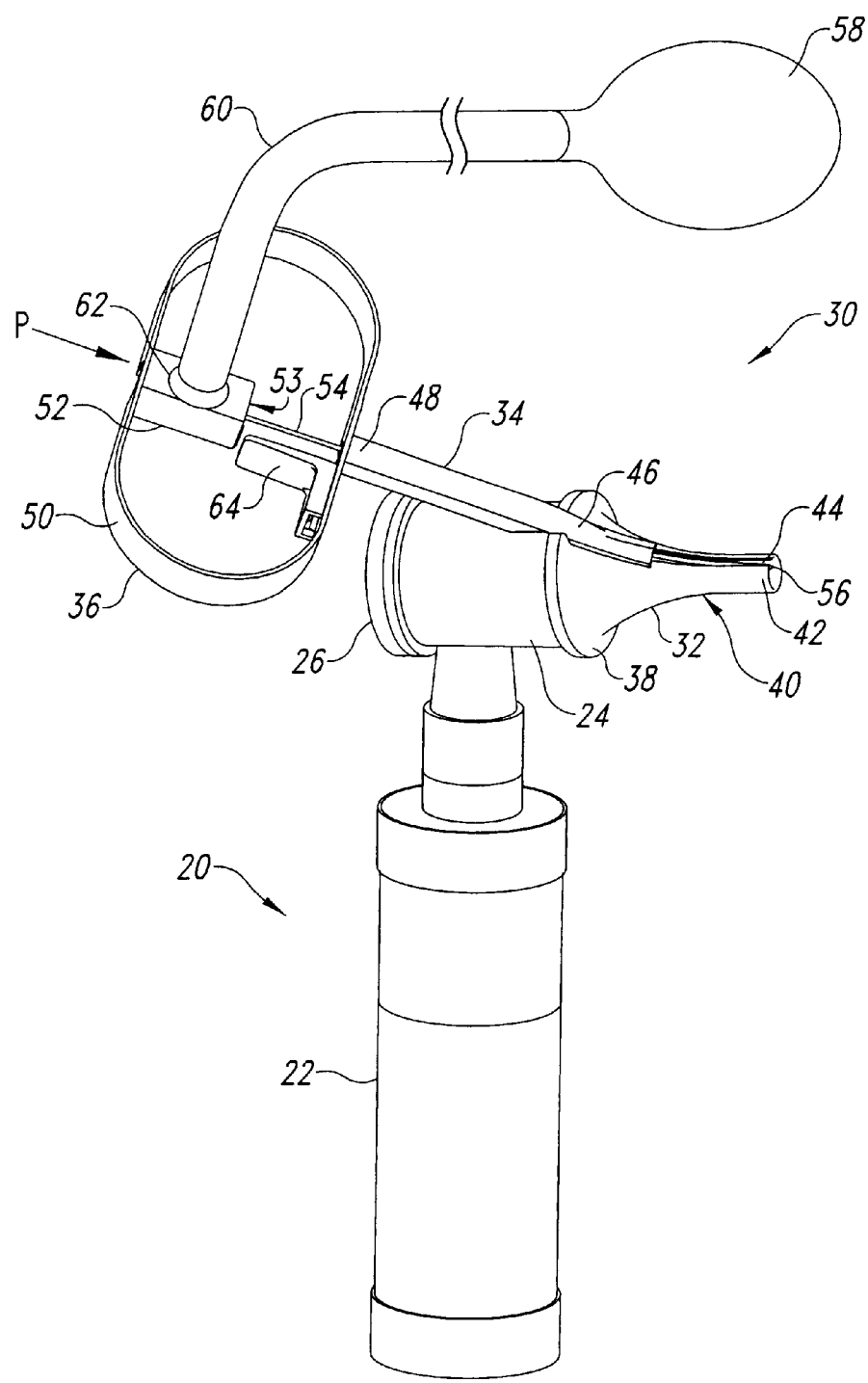
FIG. 1 is an isometric view of an otoscope and an apparatus for performing medical procedures in the external auditory canal and middle ear space according to one embodiment of the present invention.

FIG. 1 illustrates an otoscope 20 engaged with an apparatus 30 for performing medical procedures in a patient's external auditory canal and middle ear space. The illustrated otoscope 20 has an elongated, generally cylindrical body 22 configured to be comfortably held in one hand by the practitioner. The otoscope 20 also has a head 24 and an eye-piece 26. The eye-piece 26 is configured to allow the practitioner to peer through the head 24 and into the ear canal (see FIG. 10). As generally understood in the art, the otoscope 20 can also have a magnifying lens, lights for illuminating the outer ear canal, or other commonly understood features.

The illustrated apparatus 30 has a speculum 32, an elongated arm 34, and an actuator or handle 36. A proximal end 38 of the speculum 32 abuts the head 24 of the otoscope 20. A neck 70 (FIG. 3) on the speculum is engaged with a complementary mouth 72 (FIG. 3) in the head 24 to pressure fit the apparatus 30 to the head of the otoscope 20. The speculum 32 has a generally tapered sidewall 40 that extends from the proximal end 38 at which the sidewall has a diameter roughly equivalent to that of the head 24, to a distal end 42 at which the diameter of the sidewall is reduced to fit within a portion of the patient's ear canal. In the illustrated embodiment, the distal end 42 of the speculum 32 has an elongated opening 44 that extends from the distal end 42 toward the proximal end 38 of the speculum 32. As discussed in further detail below, the opening 44 allows a probe or needle 54 placed against the sidewall 40 of the speculum 32 to pass from a point external of the sidewall of the speculum to a point internal thereto to align the probe or needle with the patient's ear canal. For convenience, applicant uses the term "probe" herein to refer to either a probe or a needle.

A distal end 46 of the arm 34 is attached to the proximal end 38 of the speculum 32. A proximal end 48 of the arm 34 is connected to the handle 36. In the illustrated embodiment, the distal end 46 of the arm 34 is removably connected to the speculum 32, while the proximal end 48 of the arm is fixedly attached to the handle 36. It is understood, however, that the arm 34 can be attached by a variety of means to the speculum 32 and the handle 36. At the same time, the arm 34 can instead be integrally formed as a single piece with the speculum 32 and/or the handle 36.

The illustrated handle 36 is molded in the form of an oval band 50. The band 50 has a generally rectangular cross section that is sufficiently tall to provide the handle with enough structural integrity to maintain its shape, but at the same time sufficiently thin to allow the handle 36 to be compressed when a force is exerted on the handle in direction "P". The portion of the handle 36 opposite the arm 34 has a housing 52. When the apparatus 30 is configured as illustrated in FIG. 1, the probe 54 extends from the housing 52, through the arm 34 and along the sidewall 40 of the speculum 32, and a distal end 56 of the probe terminates at a point within the distal end 42 of the speculum. The probe 54 moves with the housing 52 and, consequently, movement of the housing in direction P results in movement of the distal end 56 of the probe with respect to the distal end 42 of the speculum 32.

The side of the housing 52 closest to the arm 34 terminates in a surface 53. The surface 53 is spaced apart from the opposing side of the handle 36 by a distance that corresponds to the maximum distance that the distal end 56 of the probe 54 can be extended out of the distal end 42 of the speculum 32. When the handle 36 is compressed by this maximum distance, the surface 53 of the housing 52 contacts the handle 36, preventing the actuator from being further compressed. The original distance between the surface 53 and the handle 36 can be selected or varied to provide the practitioner with a known maximum extension distance.

A hollow bulb 58 is coupled by a section of tubing 60 to the probe 54. The tubing 60 extends between the bulb 58 and a nipple 62 projecting from the housing 52. The bulb 58 can be used to produce a suction at the distal end 56 of the probe 54, or to expel a fluid from the distal end of the probe. Other embodiments of the invention can be made without the bulb 58, tubing 60, or nipple 62. In such cases, the probe 54 would be used merely to puncture an object, such as an eardrum. The apparatus in that instance would not be used to aspirate fluid from the middle ear.

Figure 2:
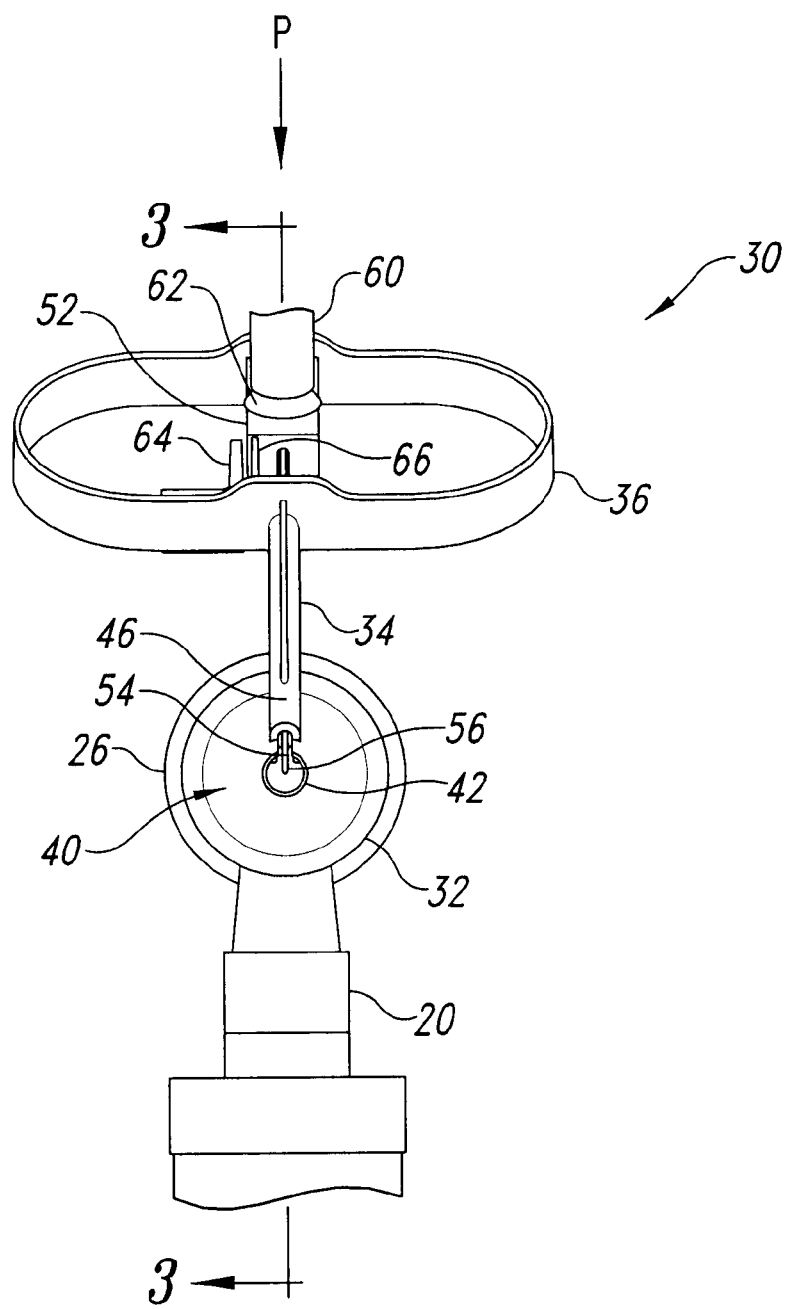
FIG. 2 is a front elevation view of a portion of the otoscope and apparatus of FIG. 1.

FIG. 2 further illustrates a portion of the otoscope 20 and the apparatus 30 of this embodiment of the invention. From this perspective, it can be seen that the distal end 46 of the arm 34 has a generally C-shaped cross section. When the arm 34 is attached to the sidewall 40 of the speculum 32, the open portion of the C-shaped cross section contacts the sidewall to help retain and guide the probe 54 therebetween. The distal end 56 of the probe 54 terminates within a boundary defined by the sidewall 40 of the speculum 32.

A safety latch 64 is attached to the portion of the handle 36 closest to the arm 34, and is movable in a lateral direction with respect to direction P. As illustrated in FIG. 2, the safety latch 64 is spaced laterally with respect to the housing 52 to allow the housing to move in direction P without restriction. When the safety latch 64 is moved laterally toward the center of the handle 36 (see, e.g., FIG. 11), the safety latch limits the movement of the housing in direction P. This obstruction prevents the distal end 56 of the probe 54 from projecting from the distal end 42 of the speculum 32. A safety stop 66 is illustrated on the housing 52 to resist the safety latch 64 from sliding laterally off of the housing 52. It is envisioned by the inventor that many variations of safety mechanisms can be used in the place of the illustrated mechanism.

Figure 3:
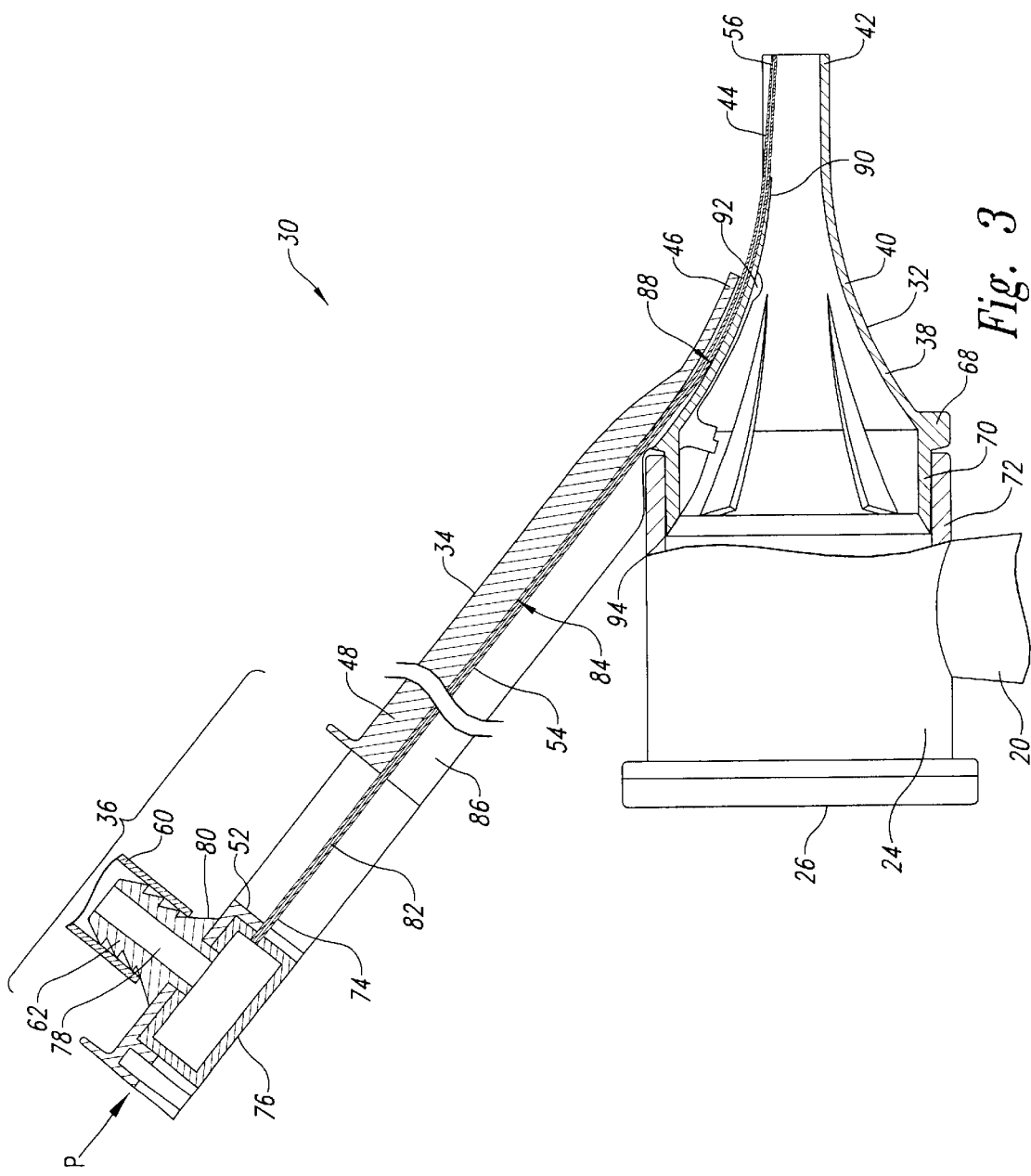
FIG. 3 is a sectional, side elevation view of the portion of the otoscope and apparatus of FIG. 2, as viewed along Section 3—3.

As illustrated in the sectional view of FIG. 3, the proximal end 38 of the speculum 32 terminates in a shoulder 68. The neck 70 projects in the proximal direction from the shoulder 68 for engagement with the mouth 72 within the head 24 of the otoscope 20. In the illustrated embodiment, the neck 70 slides into the mouth 72 and a pressure fit resists disengagement of the apparatus 30 from the otoscope 20.

One possible path of the probe 54 can be clearly seen in FIG. 3. A proximal end 74 of the probe 54 terminates at a hub 76 retained within the housing 52. The hub 76 in the illustrated embodiment is closely retained within the housing 52 by a raised-ring feature 80 on the nipple 62, which effectively prevents the hub from moving with respect to the housing. The nipple 62 has a hole 78 therethrough for transferring the pressure or suction from the bulb (FIG. 1) through the probe 54.

The probe 54 has a bore 82 extending longitudinally therethrough from the proximal end 74 to the distal end 56. The bore 82 is in fluid communication with the hub 76 and nipple 62. The probe 54 initially extends from the hub 76 in the P direction. When the probe reaches the proximal end 48 of the arm 34, the probe may contact an internal surface 84, and extends between two opposing, internal sidewalls 86 of the arm. The internal surface 84 and the internal sidewalls 86 are generally aligned with the P direction to guide the probe 54 between the handle 36 and the speculum 32. In the illustrated embodiment, near the distal end 46 of the arm 34, the internal surface 84 bends away from the probe 54. The probe 54 extends away from the arm 34 and contacts the proximal end 38 of the speculum 32 at a groove 88. The groove guides the probe 54 from the proximal end 38 of the speculum 32 to a terminal point 90 intermediate the proximal and distal ends of the speculum. The probe 54 of this embodiment is bent by the groove 88, and retains a residual curvature during use. It is understood that different probes can be used which do not exhibit such memory, and which still embody the spirit of the present invention. At the terminal point 90, the groove 88 is aligned to direct the probe 54 to a location slightly within the sidewall 40 of the speculum 32 at a location proximate the speculum's extreme distal end 42. In this position, the distal end 56 of the probe 54 is aligned for insertion into the outer ear canal, but is spaced from the centerline of the speculum to avoid obstructing the view of the practitioner.

The arm 34 is removably attached to the speculum 32 by a pair of fingers 92 at the extreme distal end 46 of the arm, and a pair of tabs 94 positioned to align with the proximal end 38 of the speculum. As discussed below, the speculum has a pair of complementary slots for receiving the fingers 92 and the tabs 94, and for thereby retaining the arm 34 to the speculum 32.

Figure 4:
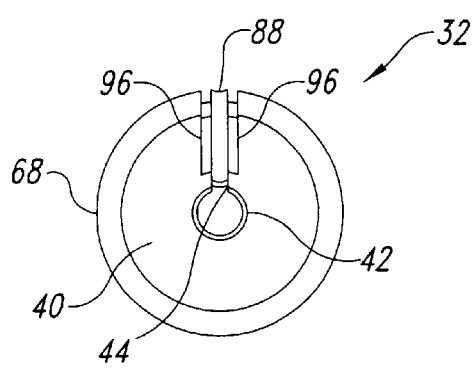
FIG. 4 is a front elevation view of a speculum from the apparatus of FIG. 1.
Figure 5:
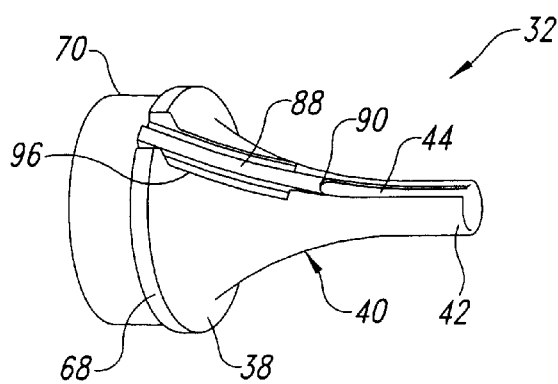
FIG. 5 is an isometric view of the speculum of FIG. 4.
Figure 6:
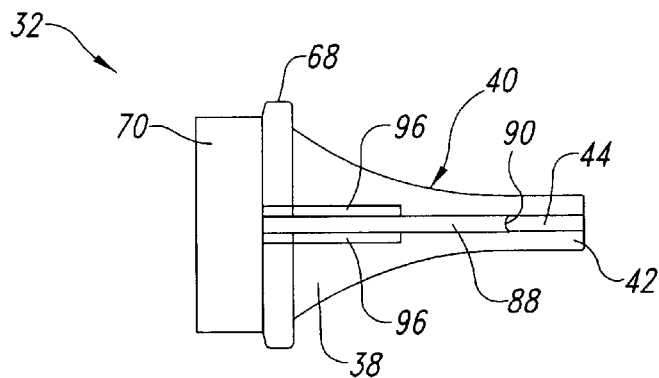
FIG. 6 is a top plan view of the speculum of FIG. 4.

FIGS. 4–6 further illustrate the speculum 32 of the present embodiment. The groove 88 has a curved cross section and extends from the proximal end 38 of the sidewall 40 to the terminal point 90 between the proximal end and the distal end 42 of the sidewall. The groove is shaped to receive the probe 54 (FIG. 1) from the side, and to guide the probe from the proximal end 38 of the speculum 32 to the terminal point 90. The angle of the groove 88 at the terminal point 90, as discussed above, is designed to direct the probe 54 through the opening 44 in the sidewall 40 to a point internal to the distal end 42 of the speculum 32. The arcuate shape of the groove 88 helps retain the probe 54 in proper alignment. The groove could instead have a wide variety of slopes, such as a V-shape or square channel.

A slot 96 can be located on each lateral side of the groove 88. The slot 96 is elongated and shaped to receive the arm 34 (FIG. 3), as discussed above.

Figure 7:
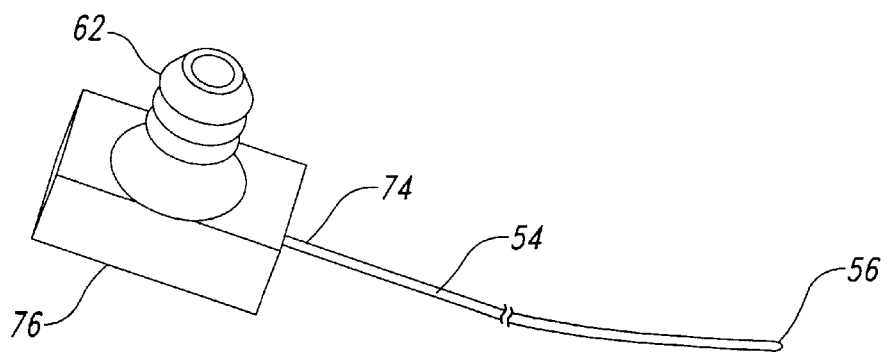
FIG. 7 is an isometric view of a probe from the apparatus of FIG. 1.
Figure 10:
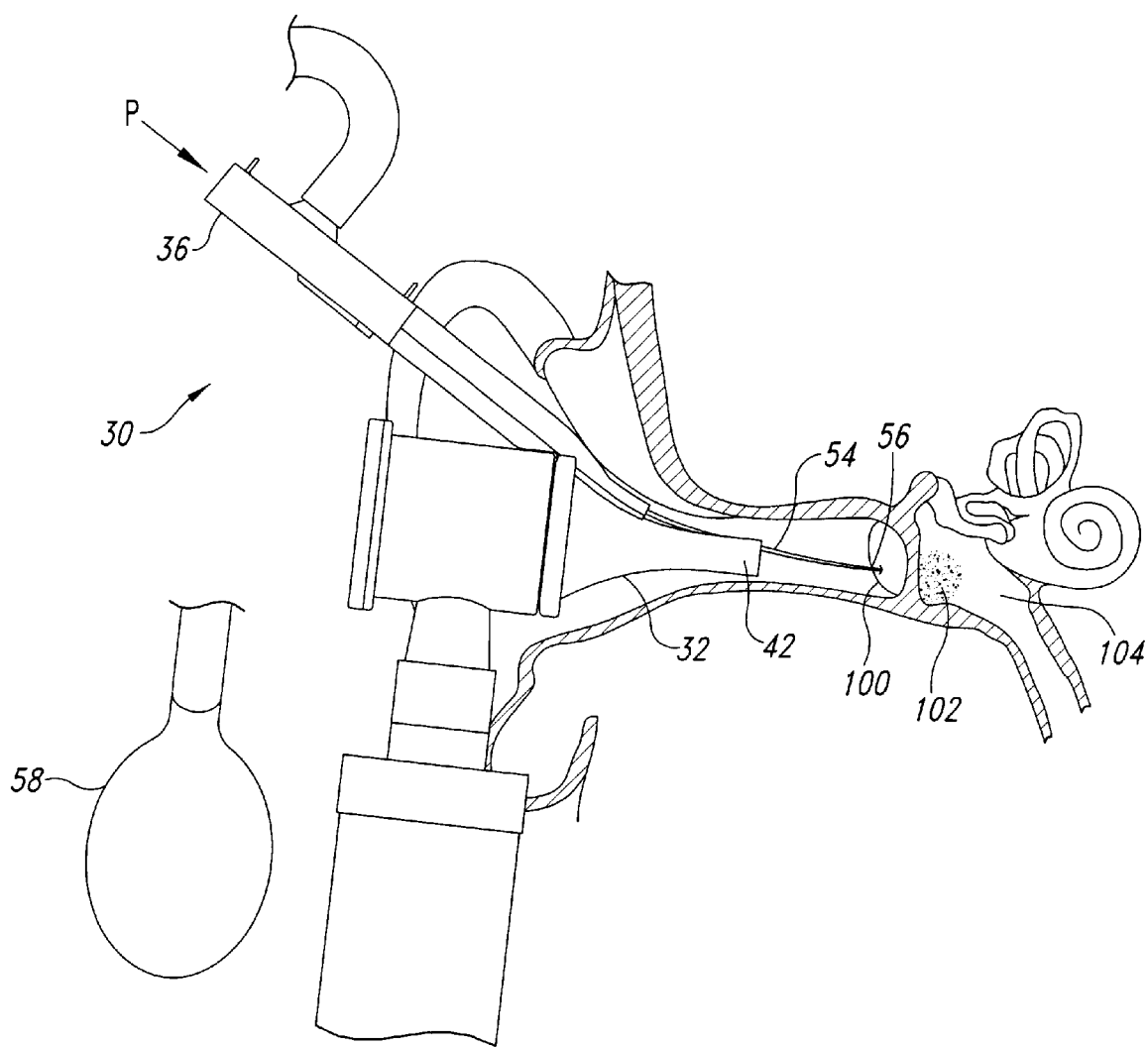
FIG. 10 is a side elevation view of the portion of the otoscope and apparatus of FIG. 9, illustrating a different step during the procedure.

FIG. 7 further illustrates the probe 54. The illustrated probe 54 is an elongated, flexible member that is sufficiently stiff to retain its linear shape when in a relaxed state, sufficiently flexible to readily conform to the shapes of objects it comes into contact with, and which is permanently deformed when bent. Accordingly, as described above and shown in FIG. 3, when the probe 54 extends from the housing 52 to the arm 34, the probe maintains a substantially linear shape. As the probe 54 extends through the arm 34 the probe maintains its generally linear shape in the embodiment illustrated in FIG. 3. When the probe 54 spans the void between the distal end 46 of the arm 34 and the groove 88 in the speculum 32 the probe tends to maintain its substantially linear shape. The probe 54 then follows the contour of the groove 88 to its terminal point 90. The portion of the needle that contacts groove 88 may be permanently deformed to an extent which creates a slight, permanent curvature in the needle. As a result, instead of continuing in the direction dictated by the termination point 90 of the groove 88, the needle bends to a point at which it is generally parallel with the practitioner's line of sight (FIG. 10).

The inventor envisions many variations to the shape of the groove 88 and the angle of the terminal point 90 to accommodate the particular needs of the practitioner, different types of probes, as well as other factors. In other variations, it is envisioned that the arm 34 can be contoured to best suit the practitioner and, as a result, the probe 54 will bend with the contoured arm to follow the shape of the arm. Likewise, in still other variations, the probe can be bent prior to insertion into the apparatus 30, creating a preferred radius of curvature based on the shape of a patient's ear canal or other factors.

Figure 8:
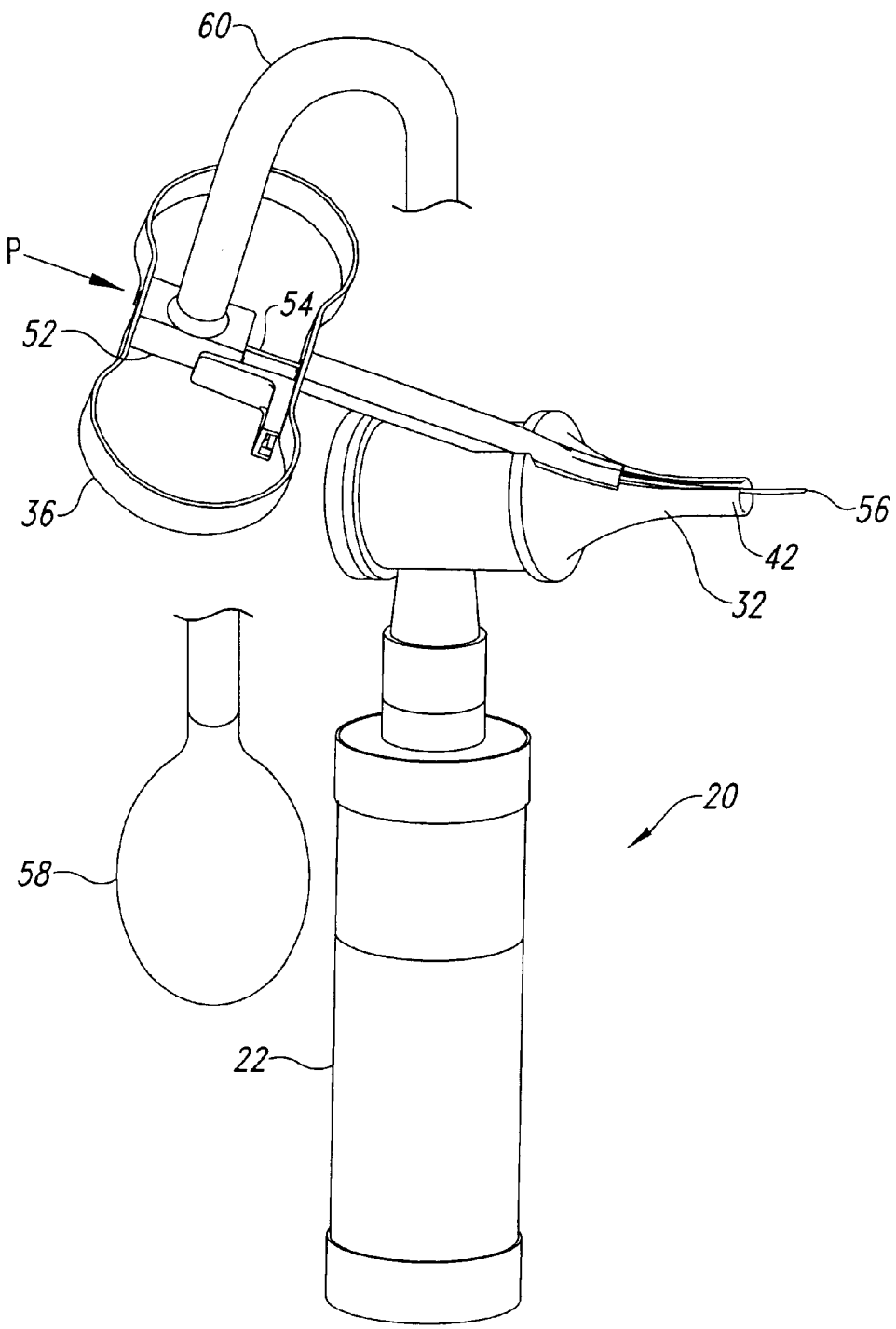
FIG. 8 is another isometric view of the otoscope and apparatus of FIG. 1, shown in an alternate operating position.

FIG. 8 illustrates the present embodiment of the invention configured for use during a particular procedure. In this particular configuration, the handle 36 has been depressed in the P direction, urging the housing 52 and, in turn, the probe 54 in the P direction. As a result, the distal end 56 of the probe 54 projects beyond the distal end 42 of the speculum 32.

Also illustrated in FIG. 8 is the configuration of the bulb 58 and tubing 60 during one particular procedure. In this configuration, the practitioner can hold the bulb 58 and the body 22 of the otoscope 20 with the same hand, freeing up the other hand for depression of the handle 36. The handle 36 can be squeezed with only three fingers, leaving two other fingers and the palm of the hand free for placement against the patient's head to retain the patient's head in a fixed position. As a result, this particular configuration can allow the practitioner alone to control the patient's head, insert the speculum 32 into the ear canal, project the distal end 56 of the probe 54 down the ear canal and puncture the eardrum, release the bulb 58 to draw a specimen of fluid from the middle ear, then release the compression on the handle to retract the needle. Although a practitioner need not perform the procedure alone, this configuration can nonetheless be useful.

Figure 9:
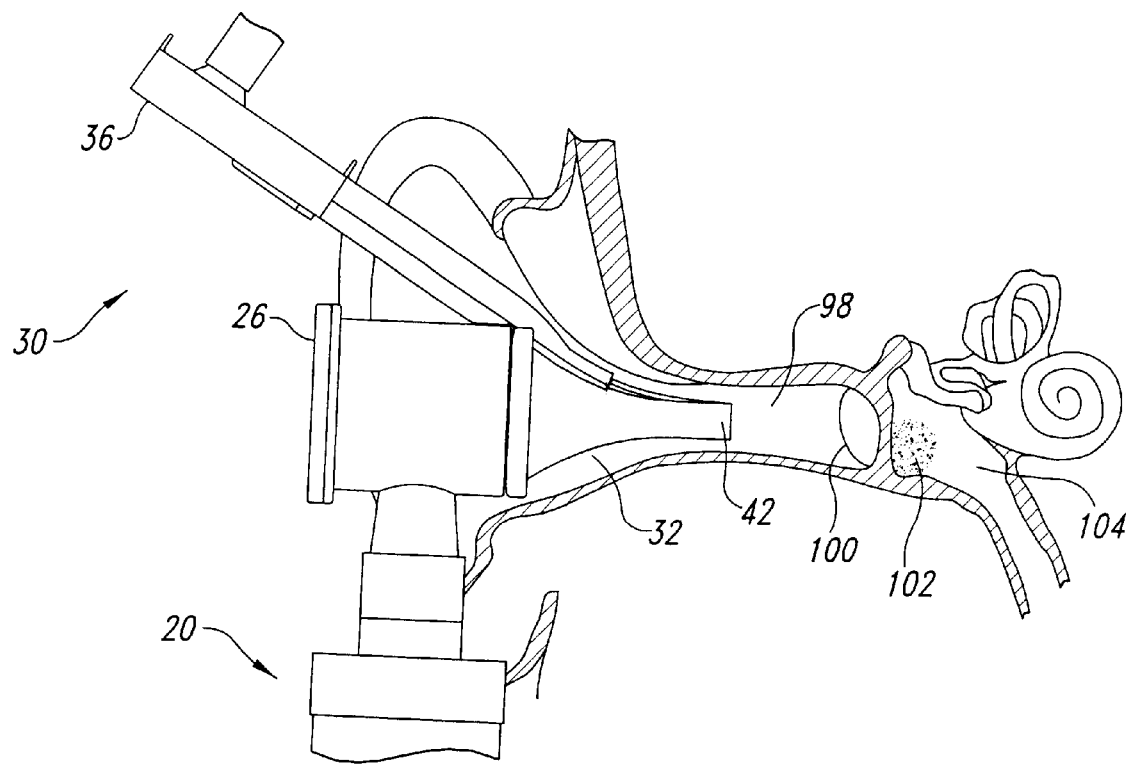
FIG. 9 is a side elevation view of a portion of the otoscope and apparatus of FIG. 1, illustrating a step during a procedure according to the present invention.

FIG. 9 illustrates the otoscope 20 and apparatus 30 of the present embodiment of the invention positioned for use during one step of a particular procedure. The distal end 42 of the speculum 32 is partially inserted into an ear canal 98 with the eyepiece 26 aligned to allow the practitioner to see down the length of the ear canal. The distal end 42 of the speculum 32 is spaced apart from an eardrum 100 separating the ear canal 98 from a middle ear 104. In this particular illustration, the middle ear 104 contains a fluid 102 exerting pressure on the eardrum 100. The practitioner consequently may desire puncturing the eardrum 100 to allow the fluid 102 to drain from the middle ear 104, and/or may desire taking a sample of the fluid 102.

As illustrated in FIG. 10, depression of the handle 36 along direction P results in the distal end 56 of the probe 54 projecting beyond the distal end 42 of the speculum 32. The amount of resiliency of the handle and the distance between the distal end 42 of the speculum 32 and the eardrum 100 can be modified to accommodate the practitioner's preferences. With the proper range of motion and resiliency in the handle 36, the apparatus 30 can allow the practitioner to comfortably project the distal end 56 of the probe 54 into the eardrum 100. Under such circumstances, the practitioner may be able to perform a more precise procedure.

While in this position, the bulb 58 can be expanded to draw some of the fluid 102 out of the middle ear 104. The practitioner can retract the probe 54 from the eardrum 100 by merely reducing the pressure on the handle 36, and can allow pressure in the middle ear 104 to express some of the fluid 102.

Certain embodiments of the present invention have a number of advantages over devices and methods of the prior art. For example, the invention is configured to be quickly and easily assembled. The needle or probe engages the speculum against its exterior surface. Consequently, the needle need not be threaded through a guide. Instead, the needle or probe can be laid into an open channel in the arm, locked into place by inserting the hub into the housing in the handle, and engaged by merely laying the arm against the exterior wall of the speculum. The arm can then be snapped into place and the device is ready for use. Another embodiment would require only that the needle be passed through a relatively large aperture in the speculum sidewall prior to laying the arm against the exterior wall of the speculum and snapping it into place.

In addition, devices according to embodiments of the present invention can be more precise than those used in the prior art. The resilient handle fixedly retains the hub of the needle or probe therein, causing the movement of the needle to be controlled entirely by the depression of the handle. This actuating feature allows the practitioner to project the needle from the speculum by merely squeezing the handle against the natural resistance of the resilient material. The resilient material's resistance may give the practitioner a better feel for and control of the movement of the probe.

Embodiments of the invention may also allow a single individual to insert the speculum into the patient's outer ear canal, puncture the patient's eardrum, draw a specimen of fluid from the middle ear, and hold the patient's head during the entire procedure.

Embodiments of the invention may also allow the practitioner to use a single apparatus with both of the currently standard otoscopic heads.

Figure 11:
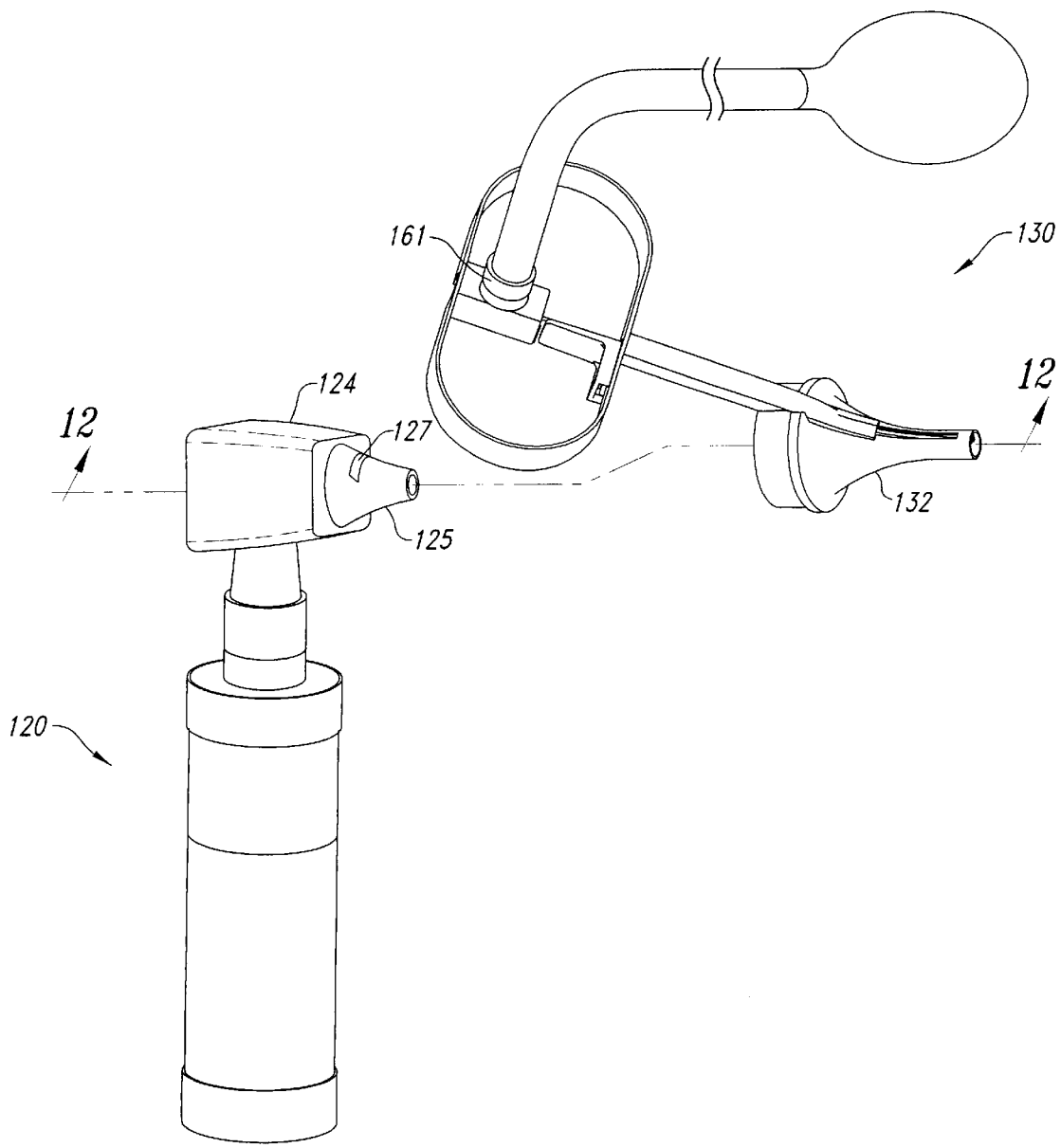
FIG. 11 is an exploded isometric view of another apparatus and an alternate type of otoscope according to another embodiment of the present invention.

FIG. 11 illustrates another apparatus 130 aligned for engagement with an otoscope 120 having a rectangular, "notched style" head 124. In this particular embodiment, the head 124 of the otoscope 120 has a reduced diameter compared to the previous otoscope 20, and incorporates an extended mounting surface 125. The speculum 132 is sized to fit over the mounting surface 125. The extended mounting surface 125 is tapered to complement the inner dimensions of the speculum 132. The tapered mounting surface 125 has a laterally angled locking notch 127 cut into its surface.

Figure 12:
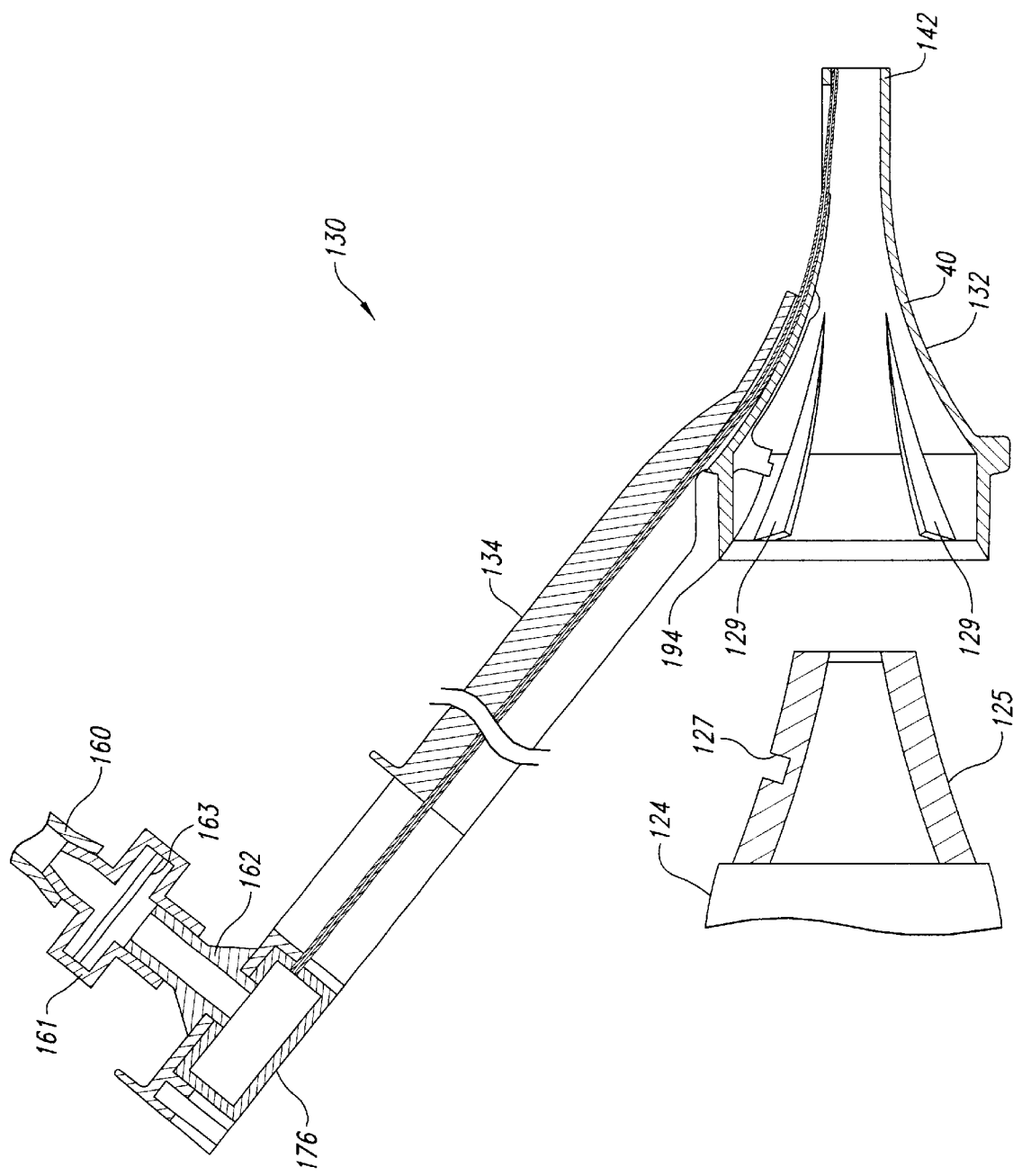
FIG. 12 is a side sectional view of a portion of the apparatus and otoscope of FIG. 11, as viewed along Section 12—12.
Figure 13:
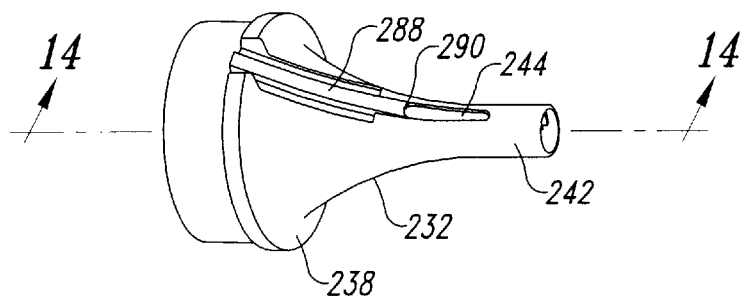
FIG. 13 is an isometric view of another speculum according to another embodiment of the invention.

FIG. 12 illustrates an arm 134 with integral tabs 194. The securing feature for the notched style heads is created only upon assembly of the arm 134 to the speculum 132, wherein the tabs on the arm extend into the speculum interior. The tabs 194 are aligned to engage the locking slot 127 on the extended conical mounting surface 125 of the diagnostic head 124. Ribs 129 on the speculum interior contact the mounting surface 125 of the diagnostic head to maintain proper alignment between the speculum 132 and the head 124.

The tabs 194 engage the locking notch 127 as the apparatus 130 is pressed onto the mounting surface 135. A clockwise twisting motion of the apparatus 130 threads and pulls the apparatus onto the mounting surface 125, such that the resultant threaded fit resists disengagement of the apparatus from the otoscope 120.

This embodiment also illustrates a filter 161 located between the tubing 160 and the nipple 162. The filter 161 has a disc-shaped housing, incorporating a hydrophobic, microbial filter element 163. The size, shape and element used can be varied to suit particular needs or practitioner preferences, as generally understood in the art to prevent contamination of the tubing 160 or bulb. The tapered outer diameter of the nipple 162 slides into a corresponding tapered inner diameter in the filter 161, creating a pressure fit which securely holds the filter 161 to the hub 176. The distal end of the filter 161 also features a tapered outer diameter that accommodates attachment of the tubing 160 via a pressure fit. The connectors used to attach the filter 161 to the device can vary as generally understood in the art. For example, Luer connectors or other suitable connectors can be substituted for those illustrated.

FIGS. 13–16 illustrate a speculum 232 according to yet another embodiment of the present invention. In this particular embodiment, a groove 288 extends from a proximal end 238 of the speculum 232 to a terminal point 290 as generally discussed above. An aperture 244 is located distally with respect to the terminal point 290. The aperture 244 extends a portion of the distance between the terminal point 290 and the distal end 242 of the speculum 232. Accordingly, the distal end 242 of the speculum 232 has a closed cross section. The groove 288 is shaped to direct a probe (not shown) from the terminal point 290, through the aperture 244, and out the distal end 242 of the speculum 232.

Figure 14:
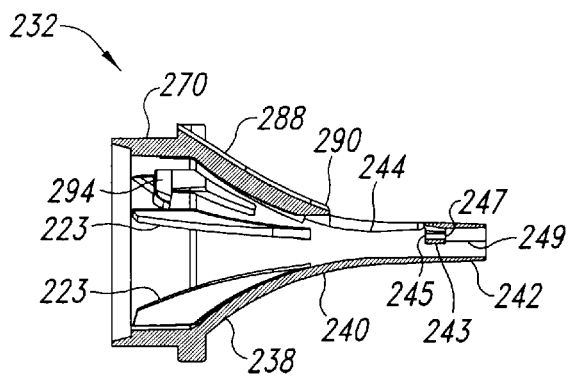
FIG. 14 is a sectional elevation view of the speculum of FIG. 13, as viewed along Section 14—14.
Figure 15:
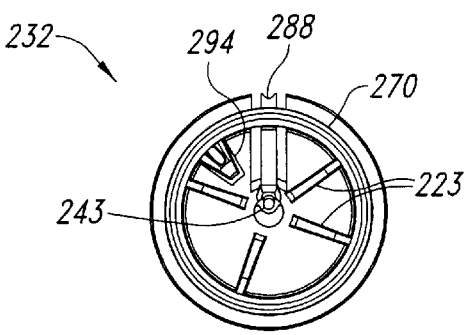
FIG. 15 is a rear elevation view of the speculum of FIG. 13.
Figure 16:
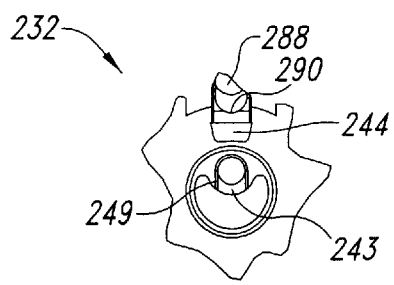
FIG. 16 is a front elevation view of a portion of the speculum of FIG. 13.

As illustrated in FIGS. 14 and 15, an internal projection 294 extends inward from the proximal end 238 of the speculum. Similar to that discussed above, the projection 294 is sized, shaped and positioned to engage a locking slot 127 (FIG. 12) on a notched style otoscope head 124 (FIG. 12). The illustrated projection 294 is integrally formed with the speculum 232. A number of internal ribs 223 also project internally from the interior surface of the speculum 232. These ribs 223 conform with the extended mounting surface 125 on the otoscope 124 (FIG. 12), retaining the speculum 232 in the proper alignment. A neck 270 projects in the proximal direction from the proximal end 238 of the speculum 232. The neck 270 is sized to engage the mouth 72 on the first illustrated otoscope 20 (see FIG. 3). As a result, the speculum 232 of this particular embodiment can engage both types of otoscope heads.

A guide ring 243 is positioned distally of the aperture 244, and extends between a proximal end 245 and a distal end 247. The proximal end 245 of the guide ring 243 is adjacent the aperture 244, and the distal end 247 of the guide ring is located between the aperture and the extreme distal end 242 of the speculum 232. Between the distal end 247 of the guide ring 243 and the extreme distal end 242 of the speculum 232, a channel 249 is formed interior to the speculum wall 240.

During operation, a probe 54 (FIG. 7) extends from the proximal end 238 of the speculum 232, along the groove 288, and into the aperture 244. The probe 54 extends through the guide ring 243 and terminates within the interior of the speculum 232 when the actuator is relaxed, as discussed above. When the actuator is depressed, the distal end 56 of the probe 54 projects beyond the distal end 242 of the speculum 232. The guide ring 243 retains the distal end 56 of the probe 54 in the proper vertical alignment, and the channel 249 retains the distal end of the probe in the desired horizontal alignment. The size, shape and angle of the guide ring 243 and channel 249 can be modified to satisfy particular needs or desires of the practitioner.

Figure 17:
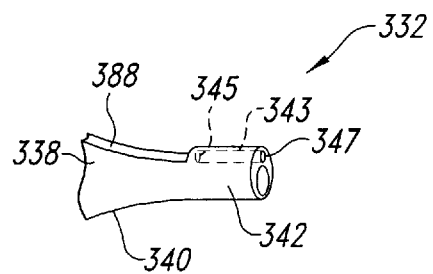
FIG. 17 is an isometric view of a portion of a speculum according to another embodiment of the present invention.

FIG. 17 illustrates still another speculum 332 according to still another embodiment of the present invention. In this particular embodiment, a groove 388 extends from a proximal end 338 of the speculum 332 toward a distal end 342 of the speculum. The distal end 342 of the speculum 332 has a closed cross section. A guide tube 343 is formed on the exterior surface 340 of the speculum 332, in alignment with the groove 388. The open proximal end 345 of the guide tube 343 is adjacent the groove 388, and the open distal end 347 of the guide tube is adjacent the distal end 342 of the speculum 332. The flexible probe (not shown) passes from the groove 388 into the proximal end 345 of the guide tube 343. The probe can be further extended beyond the distal end 347 of the guide tube 343, into the ear canal, while being positionally controlled by the guide tube 343. The guide tube 343 can be integral with or attached to the sidewall 340 of the speculum 332, and is located completely external to the speculum.

Figure 18:
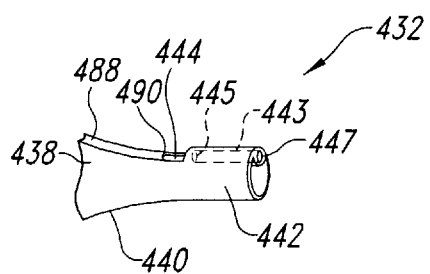
FIG. 18 is an isometric view of a portion of another speculum according to another embodiment of the present invention.

FIG. 18 illustrates still another speculum 432 according to still another embodiment of the present invention. In this particular embodiment, a groove 488 extends from a proximal end 438 of the speculum 432 to a terminal point 490, as generally discussed above. An aperture 444 is located distally with respect to the terminal point 490. The aperture 444 extends a portion of the distance between the terminal point 490 and the distal end 442 of the speculum 432. Accordingly, the distal end 442 of the speculum 432 has a closed cross section. A guide tube 443 is incorporated into the distal end 442 of the speculum sidewall 440 in such a fashion that it longitudinally bisects the circumferential plane of the sidewall. The guide tube 443 is located partly on the interior and partly on the exterior of the speculum 432, in alignment with the groove 488 and aperture 444. The open proximal end 445 of the guide tube 443 is adjacent the aperture 444. The open distal end 447 of the guide tube 443 is adjacent the distal end 442 of the speculum 432. The flexible probe (not shown) passes from the groove 488 into the proximal end 445 of the guide tube 443. The probe can be extended beyond the distal end 447 of the guide tube 443, into the ear canal, while still being positionally controlled by the guide tube 443.

Figure 19:
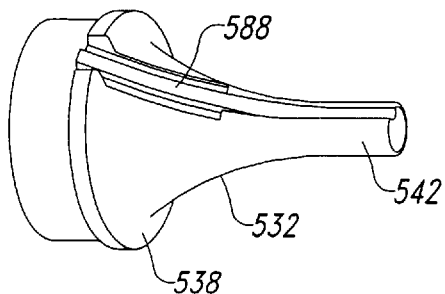
FIG. 19 is an isometric view of still another speculum according to still another embodiment of the present invention.

FIG. 19 illustrates still another speculum 532 according to still another embodiment of the present invention. In this particular embodiment, a groove 588 extends the entire distance from a proximal end 538 of the speculum 532 to a distal end 542 of the speculum. The groove 588 is sufficiently deep to allow the probe (not shown) to be completely contained within the extended circular boundary defined by the distal end 542 of the speculum 532.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A speculum for use in connection with an otoscope for performing a procedure using one of an elongated probe and needle, the speculum comprising:

a sidewall generally tapered in shape, the sidewall having an exterior surface and proximal and distal ends, the proximal end of the sidewall being configured for engagement with the otoscope, the distal end of the sidewall having configured for insertion into an ear canal, the exterior surface of the sidewall having an open groove thereon opening outward from the speculum and extending from the proximal end of the sidewall toward the distal end of the sidewall, the sidewall further having an opening therethrough located distally of the groove,: the groove being sized and shaped to receive a needle/probe at the proximal end of the sidewall, and the groove being; aligned to direct the needle/probe from the proximal end of the sidewall, through the opening, and into the ear canal beyond the distal end of the sidewall.

2. The speculum of claim 1 wherein the opening in the sidewall is a slot extending from the distal end of the sidewall toward the proximal end of the sidewall.

3. The speculum of claim 1 wherein the opening in die sidewall is an aperture.

4. The speculum of claim 1, further comprising, a guide tube positioned proximate the distal end of the speculum and aligned with the groove to direct the needle/probe along the ear canal, the opening in the sidewall being an aperture having proximal and distal ends, the proximal end of the aperture abutting the groove, the distal end of the aperture abutting the guide tube.

5. The speculum of claim 1, further comprising: a guide tube positioned proximate the distal end of the speculum and aligned with the groove to direct the needle/probe along the ear canal, the operating in the sidewall being an aperture having proximal and distal ends, the proximal end of the aperture abutting the groove, the distal end of the aperture being spaced apart from the guide tube.

6. The speculum of claim 1, further comprising a guide tube positioned proximate the distal end of the speculum and aligned to direct the needle/probe along the ear canal, the opening in the sidewall being an aperture having proximal and distal ends, the proximal end of the aperture abutting the groove, the distal end of the aperture abutting the guide tube a portion of the guide tube being internal to the sidewall of the speculum and a portion of the guide tube being external to the sidewall of the speculum.

7. The speculum of claim 1, further comprising a coupling element for receiving a guide member for guiding the probe along at least a portion of the groove.

8. The speculum of claim 1, further comprising at least one slot extending through the sidewall of the speculum, the at least one slot being configured to receive a portion of a guide member for guiding the probe along at least a portion of the groove.

9. The speculum of claim 1, further comprising a pair of slots positioned on opposing sides of the groove for receiving a complementary pair of tabs on a guide member for guiding the probe along at least a portion of the groove.

10. The speculum of claim 1, further comprising a guide member removably coupled to the sidewall of the speculum, the guide member being configured to retain the probe at least substantially in the groove.

11. An apparatus for inserting one of a flexible needle and probe into an ear canal, the apparatus comprising:
    a speculum having a sidewall generally tapered in shape, the sidewall having proximal and distal ends, the proximal end of the sidewall being configured for engagement with an otoscope, the distal, end of the sidewall being configured for insertion into the ear canal; and
    an actuator having proximal, and distal portions, the distal portion of the actuator being coupled to the speculum, the proximal portion of the actuator being movable with respect to the distal portion; of the actuator, the proximal portion of the actuator being configured to fixedly retain; a portion of a needle/probe, thereto, and the distal portion of the actuator being configured to direct the needle/probe along the sidewall of the speculum toward the speculum's distal end.

12. The apparatus of claim 11 wherein the distal portion of the actuator is conformed to at least a portion of the sidewall to form a guide therebetween.

13. The apparatus of claim 1 further comprising an opening in the sidewall of the speculum, and wherein a guide is aligned with the opening to direct the needle/probe through the opening and into the speculum.

14. The apparatus of claim 11 further comprising a slot extending from the distal end of the sidewall toward the proximal end of the sidewall, and wherein a guide is aligned with the slot to direct the needle/probe through the slot and into the speculum.

15. The apparatus of claim 11 wherein an exterior surface of the sidewall has a groove thereon extending from the proximal end of the sidewall toward the distal end of the sidewall, the groove being aligned to direct a distal end of the needle/probe toward the distal end of the sidewall, and wherein the distal portion of the actuator is conformed to at least a portion of the sidewall to form a guide between the distal portion of the actuator and the groove.

16. The apparatus of claim 11 wherein the actuator is removably coupled to the speculum.

17. The apparatus of claim 11 wherein the sidewall of the speculum has a guide thereon and a distal portion of the guide terminates at a central location between the proximal and distal ends of the sidewall of the speculum.

18. The apparatus of claim 11 wherein the proximal portion of the actuator is resiliently movable with respect to the distal end of the actuator.

19. The apparatus of claim 11 wherein the distal portion of the actuator is coupled to the proximal end of the sidewall, and wherein a guide is conformed to direct the needle/probe from the proximal end of the sidewall toward the distal end of the sidewall.

20. The apparatus of claim 19 further comprising an opening in the sidewall of the speculum, and wherein the guide is aligned with the opening to direct the needle/probe from the proximal end of the sidewall, through the opening and into the speculum.

21. The apparatus of claim 19 further comprising a slot extending from the distal end of the sidewall toward the proximal end of the sidewall and wherein the guide is aligned with the slot to direct the needle/probe from the proximal end of the sidewall, through the slot and into the speculum.

22. An apparatus for inserting one of a flexible needle and probe into an car canal, the apparatus comprising:
    a speculum having a sidewall generally tapered in shape, the sidewall having proximal and distal ends, the proximal end of the sidewall being configured for engagement with an otoscope, the distal end of the sidewall being configured for insertion into the ear canal, the sidewall of the speculum having an opening therethrough located between the proximal end and the distal end of the sidewall; and
    a guide coupled to the proximal end of the sidewall of the speculum, the guide being configured to direct a needle/probe along the sidewall of the speculum, through the opening and into the speculum's distal end.

23. The apparatus of claim 22 wherein a distal end of the guide terminates proximally of the opening in tie sidewall of the speculum.

24. The apparatus of claim 22 wherein the opening in the sidewall of the speculum is a slot extending from the distal end of the sidewall toward the proximal end of the sidewall.

25. The apparatus of claim 22 wherein the opening in the sidewall of the speculum is an aperture.

26. The apparatus of claim 22 further comprising an actuator having a fixed portion and a movable portion, the fixed portion of the actuator being fixedly coupled to the guide, the movable portion of the actuator being movable with respect to the fixed portion of the actuator, the movable portion of the actuator being configured to fixedly retain a portion of the needle/probe thereto.

27. An otoscopic accessory for use in performing tympanocentesis, the accessory comprising:
   a speculum having a sidewall generally tapered in shape, the sidewall having an exterior surface and proximal and distal ends, the proximal end of the sidewall being configured for engagement with an otoscope, the distal end of the sidewall being configured for insertion into an ear canal;
   a flexible needle having a shaft and a distal end, a portion of the shaft of the needle being positioned against the exterior surface of the sidewall; and
   an actuator coupled to the speculum, the actuator having proximal and distal portions, the distal portion of the actuator being closely conformed to at least the proximal end of the sidewall to form a guide between the exterior surface of the speculum and the distal portion of the actuator, the guide directing the distal end of the needle to a location within the distal end of the sidewall of the speculum, the proximal portion of the actuator being movable with respect to the distal portion of the actuator, the proximal portion of the actuator being fixedly coupled to the needle for movement with the needle between a first position in which the distal end of the needle is proximal of the distal end of the sidewall of the speculum and a second position in which the distal end of the needle projects beyond the distal end of the sidewall of the speculum.

28. The accessory of claim 27, further comprising an opening in the sidewall of the speculum, the opening being located distally of the guide, and wherein the guide is aligned with the opening to direct the needle through the opening and into the ear canal beyond the distal end of the sidewall.

29. The accessory of claim 27, further comprising a slot extending from the distal end of the speculum toward the proximal end of the speculum, and wherein the guide is aligned with the slot to direct the needle through the slot and into the ear canal beyond the distal end of the sidewall.

30. The accessory of claim 27 wherein the actuator is removably coupled to the speculum.

31. The accessory of claim 27 wherein the proximal portion of the actuator comprises a resilient member configured to fixedly retain a portion of the needle thereto, the resilient member being manually movable between the first and second positions.

32. The accessory of claim 27, further comprising a source of reduced pressure coupled to and in fluid communication with the needle for creating a suction at the distal end of the needle.

33. The accessory of claim 27, further comprising a bladder coupled to and in fluid communication with the needle for providing one of increased and decreased pressure near the distal end of the needle.

34. The accessory of clam 27, further comprising:
   a bladder coupled to and in fluid communication will the needle for providing one of increased and decreased pressure near the distal end of the needle; and
   a filter element positioned between the bladder and the needle.

35. A speculum for being alternatingly used in combination with a first otoscope having a cylindrical mouth, and with second otoscope having a tapered distal projection with a locking groove therein the speculum comprising:
   a sidewall generally tapered in shape, the sidewall having proximal and distal ends and an interior surface, the distal end of the sidewall being configured for insertion into an ear canal, the proximal end of the sidewall having at least one proximal projection sized and shaped to frictionally engage the mouth of the first otoscope when the speculum is engaged with the first otoscope, the interior surface of the sidewall having at least one internal projection projecting inwardly from the interior surface for engagement with the second otoscope, the at least one projection being positioned on the speculum to engage the locking groove when the speculum is engaged with the second otoscope.

36. The speculum of claim 35, further comprising a guide coupled to the speculum for directing a probe/needle from a point near the proximal end of the speculum to a point beyond the distal end of the speculum, the guide having at least one tab engaged with a complementary opening in the speculum, and wherein the internal projection comprises a portion of the tab of the guide.

37. The speculum of claim 35, further comprising an actuator coupled to the speculum for controllably directing a probe/needle along the sidewall of the speculum to a point beyond the distal end of the speculum, the actuator having at least one tab engaged with a complementary opening in the speculum, and wherein the internal projection comprises a portion of the tab of the actuator.

38. The speculum of claim 35 wherein the proximal projection is a unitary, substantially cylindrical neck projecting from the proximal end of the speculum.

39. The speculum of: claim 35 wherein the internal projection is integrally formed with the speculum.

40. A speculum for use in connection with an otoscope for performing a procedure using one of an elongated probe and needle, the speculum comprising;
   a sidewall generally tapered in shape, the sidewall having an exterior surface and proximal and distal ends, the proximal end of the sidewall being configured for engagement with the otoscope, the distal end of the sidewall being configured for insertion into an ear canal, the exterior surface of the sidewall having an open groove thereon extending substantially the entire length of the speculum from the proximal end of the sidewall to the distal end of the sidewall, the groove being sized and shaped to receive a needle/probe at the proximal end of the sidewall, and the groove being aligned to direct the needle/probe from the proximal end of the sidewall, through an opening, and into the ear canal beyond the distal end of the sidewall.

41. The speculum of claim 40, her comprising a guide tube having proximal and distal ends, the guide tube being sized to receive the probe/needle and aligned with the groove to guide the probe/needle into the ear canal, the proximal end of the guide tube being located between the proximal and distal ends of the speculum, and the distal end of the guide tube being at least proximate the distal end of the speculum.

42. A method for fabricating an otoscopic accessory comprising:

providing an actuator having a fixed portion and a movable portion;

attaching a probe/needle to the movable portion of the actuator; and coupling the fixed portion of the actuator to an external wall of a speculum with a portion of the probe/needle being positioned between the external wall of the speculum and the fixed portion of the actuator.

43. The method of claim 42 wherein the probe/needle has a proximal end and attaching the probe/needle to the movable portion of the actuator comprises fixing the proximal end of the probe/needle to the actuator.

44. The method of claim 42 wherein the speculum has a proximal end and coupling the fixed portion of the actuator to the speculum comprises coupling the fixed portion of the actuator to the proximal end of the speculum.

45. The method of claim 42 wherein the speculum has at least one slot therein and the fixed portion of the actuator has at least one complementary tab, and wherein coupling the fixed portion of the actuator to the speculum comprises engaging the at least one tab with the at least one slot.

* * * * *

UNITED STATES PATENT AND TRADEMARK OFFICE
CERTIFICATE OF CORRECTION

PATENT NO.       : 6,390,975 B1
DATED            : May 21, 2002
INVENTOR(S)      : Richard Walls et al.

It is certified that error appears in the above-identified patent and that said Letters Patent is hereby corrected as shown below:

Column 10,
Line 62, "sidewall having configured" should read -- sidewall being configured --.

Column 11,
Line 1, "located distally of the groove,: the groove" should read -- located distally of the groove, the groove --.
Line 3, "groove being; aligned" should read -- groove being aligned --.
Line 10, "the opening in die" should read -- the opening in the --.
Line 12, "further comprising, a guide" should read -- further comprising a guide --.
Line 18, "further comprising, a guide" should read -- further comprising a guide --.
Line 21, "ear canal, the operating" should be corrected to read -- ear canal, the opening --.
Line 54, "the distal, end" should read -- the distal end --.
Line 56, "an actuator having proximal, and" should read -- an actuator having proximal and --.
Line 59, "distal portion; of the actuator," should read -- distal portion of the actuator, --.
Line 61, "fixedly retain; a portion of a needle/probe, thereto," should read -- fixedly retain a portion of a needle/probe thereto, --.

Column 12,
Line 1, "The apparatus of claim 1" should read -- The apparatus of claim 11 --.
Line 39, "proximal end of the sidewall and wherein" should read -- proximal end of the sidewall, and wherein --.
Line 44, "into an car canal," should read -- into an ear canal, --.
Line 58, "opening in tie sidewall" should read -- opening in the sidewall --.

Column 13,
Line 59, "The accessory of claim 27," should read -- The accessory of claim 27, --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,390,975 B1
DATED         : May 21, 2002
INVENTOR(S)   : Richard Walls et al.

It is certified that error appears in the above-identified patent and that said Letters Patent is hereby corrected as shown below:

Column 13,
Lines 52-53, "fluid communication will the" should read -- fluid communication with the --.

Column 14,
Line 1, "with second otoscope" should read -- with a second otoscope --.
Line 2, "a locking groove therein the" should read -- a locking groove therein, the --.
Line 36, "The speculum of: claim" should read -- The speculum of claim --.
Line 57, "The speculum of claim 40, her" should read -- The speculum of claim 40, further --.

Signed and Sealed this

First Day of July, 2003

JAMES E. ROGAN
*Director of the United States Patent and Trademark Office*